United States Patent [19]

Doessel et al.

[11] Patent Number: 5,403,697
[45] Date of Patent: Apr. 4, 1995

[54] POSITIVE RADIATION-SENSITIVE MIXTURE AND RECORDING MATERIAL PRODUCED THEREFROM

[75] Inventors: Karl-Friedrich Doessel, Wiesbaden; Ralph Dammel, Mainz-Bretzenheim; Juergen Lingnau, Mainz-Laubenheim, all of Germany

[73] Assignee: Hoechst Aktiengesellschaft, Frankfurt am Main, Germany

[21] Appl. No.: 881,329

[22] Filed: May 7, 1992

Related U.S. Application Data

[63] Continuation of Ser. No. 785,217, Oct. 28, 1991, abandoned, which is a continuation of Ser. No. 442,394, Nov. 27, 1989, abandoned, which is a continuation of Ser. No. 243,922, Sep. 13, 1988, abandoned.

[30] Foreign Application Priority Data

Sep. 13, 1987 [DE] Germany .................. 37 30 784.3
Jun. 25, 1988 [DE] Germany .................. 38 21 585.3

[51] Int. Cl.$^6$ ................................. G03C 1/72
[52] U.S. Cl. ............................ 430/270; 430/326
[58] Field of Search .......... 430/326, 270, 281, 175, 430/189, 921; 522/35, 45, 49, 41, 52, 67

[56] References Cited

U.S. PATENT DOCUMENTS

| | | | |
|---|---|---|---|
| 3,374,160 | 3/1968 | Mao | 522/45 |
| 3,515,552 | 6/1970 | Smith | 96/35.1 |
| 3,518,175 | 6/1970 | Bell | 522/45 |
| 3,536,489 | 10/1970 | Smith | 96/28 |
| 3,754,911 | 8/1973 | Jones | 522/45 |
| 3,779,778 | 12/1973 | Smith et al. | 96/115 |
| 3,888,804 | 6/1975 | Swanholm et al. | 522/45 |
| 4,101,323 | 7/1978 | Buhr et al. | 96/35 |
| 4,247,611 | 1/1981 | Sander et al. | 430/286 |
| 4,248,957 | 2/1981 | Sander et al. | 430/270 |
| 4,266,000 | 5/1981 | Stahlhofen et al. | 430/192 |
| 4,289,845 | 9/1981 | Bowden et al. | 430/296 |
| 4,311,782 | 1/1982 | Buhr et al. | 430/270 |
| 4,368,253 | 1/1983 | Green et al. | 430/326 |
| 4,371,607 | 2/1983 | Dönges | 430/281 |
| 4,398,001 | 8/1983 | Cheng et al. | 525/502 |
| 4,404,272 | 9/1983 | Stahlhofen | 430/192 |
| 4,457,999 | 7/1984 | Stahlhofen | 430/191 |
| 4,491,628 | 1/1985 | Ito et al. | 430/176 |
| 4,496,447 | 1/1985 | Eichler et al. | 522/45 |
| 4,506,006 | 3/1985 | Rockert | 430/325 |
| 4,618,564 | 10/1986 | Demmer et al. | 430/270 |
| 4,678,737 | 7/1987 | Schneller et al. | 430/270 |
| 4,717,640 | 1/1988 | Stahlhofen | 430/192 |
| 4,863,827 | 9/1989 | Jain et al. | 430/326 |

FOREIGN PATENT DOCUMENTS

| | | | |
|---|---|---|---|
| 2216983 | 6/1984 | Australia . | |
| 0232972 | 8/1987 | European Pat. Off. | 430/270 |
| 2243621 | 3/1973 | Germany . | |
| 2342068 | 4/1974 | Germany . | |
| 2610842 | 9/1976 | Germany . | |
| 2718259 | 4/1977 | Germany . | |

OTHER PUBLICATIONS

"Journal of the Electrochemical Society", *A Sensitive Novolac-Based Positive Electron Resist*, vol. 128, 1981.

"Photographic Science and Engineering", *Crosslinkings of Polymers with Irradiating Rh, L X Ray Effect of Active Groups and a Heavy Atom on Crosslinking*, vol. 23, No. 1–6, p. 196, 1979.

Gary N. Taylor, "Solid State Technology", *X-Ray Resist Trends*, pp. 124–131, Jun. 1984.

*Primary Examiner*—Christopher D. Rodee
*Attorney, Agent, or Firm*—Foley & Lardner

[57] ABSTRACT

A positive radiation-sensitive mixture is disclosed comprising a compound which forms an acid under the action of high-energy radiation and an acid-cleavable compound, wherein the compound which forms an acid contains aromatically bound chlorine or bromine and has a $pK_a$ value of less than about 12 or is a derivative of a compound having such a $pK_a$ value. The mixture and the recording material produced therefrom have a relatively high-sensitivity and improved resolution and, in addition, exhibit no scumming after development.

23 Claims, No Drawings

POSITIVE RADIATION-SENSITIVE MIXTURE AND RECORDING MATERIAL PRODUCED THEREFROM

This application is a continuation of application Ser. No. 07/785,217, file Oct. 28, 1991, now abandoned, which is a continuation of application Ser. No. 07/442,394, filed Nov. 27, 1989, now abandoned, which is a division of application Ser. No. 07/243,922, filed Sep. 13, 1988, now abandoned.

BACKGROUND OF THE INVENTION

The present invention relates to a positive radiation-sensitive mixture containing a compound which forms an acid under the action of high-energy radiation, and an acid-cleavable compound.

In classical UV lithography, the resolution limit is determined by the wavelength of the radiation used. The constant decrease in feature sizes in chip production therefore requires new lithographic techniques for the sub-micron region, electron or X-ray radiation being employed because of their extremely short wavelength. At the same time, it has been shown that resist materials which are suitable as electron beam resists can also be employed as X-ray resist, and vice versa.

Known resist materials for this application are acrylates and methacrylates (G. M. Taylor, *Solid State Technology*, 124 (1984)). With these materials, sensitivity and structural resolution have been found to be usually contrary properties. In order for higher sensitivities to be achieved, halogens are usually incorporated into the resist. In this case, fluorine and chlorine are usually employed in positive resists, whereas it is usually bromine and iodine, besides chlorine, which are employed in negative resists (T. Yamaoka et al., *Phot. Sci. Eng.*, 23: 196 (1979)).

In general, negative resists exhibit higher sensitivity than positive resists, but, cannot simultaneously—as stated above—have a high resolution in the submicron region. On the other hand, positive methacrylate-based resists achieve high resolution, but, with the exception of polymethacrylonitrile-based resists, are not stable to the plasma etching processes used for semiconductor structuring. In turn, however, the methacrylates are not sufficiently sensitive.

The polymers having the highest radiation sensitivity known to date for electron beams or X-rays are polyalkene sulfones, in particular, polybutene-1-sulfone. The disadvantage of this class of compounds is, however, that they are less resistant to plasma etching processes; they are therefore suitable for mask production, but not for semiconductor fabrication using a mask made of this material. It has therefore been proposed to combine polyalkene sulfones with novolak resins, which, as is generally known, are resistant to plasma etching (M. J. Bowden et al., *J. Electrochem. Soc.*, 128: 1304 (1981); U.S. Pat. No. 4,289,845). However, it became apparent that the two polymers are extremely incompatible with one another, thus impairing the resolution. An attempt to improve the compatibility by admixing further components resulted in loss in sensitivity (U.S. Pat. No. 4,398,001).

Photocatalytic systems are described in DE-A-2,718,254 and DE-A-2,928,636 for use with electron-beam and X-ray radiation. In these positive systems, chlorine-containing compounds, in particular, of the substituted triazine type, are employed as compounds which form an acid under the action of actinic radiation. During structuring of these materials using electron or X-ray radiation, however, it became apparent that the edges of the resist structures are very negatively undercut after development (edge angle around 60° according to a photomicrograph using a scanning electron microscope (SEM)) and structures of less than about 2 μm can consequently no longer be resolved or reproduced or, in other cases, are extremely frayed.

In DE-A-2,928,636, as in DE-A-2,610,842, 2,3,4,5-tetrachloroaniline, inter alia, is mentioned as the chlorine-containing compound. In addition, DE-A-2,610,842 also discloses compounds which contain aliphatically-bound bromine and one compound which carries aromatically-bound bromine: 2,2',4,4',6,6'-hexabromodiphenylamine. However, it has been shown that adequately high resolution cannot be achieved using the aromatic chlorine compound, and undesired scumming occurred with the compound mentioned containing aromatically-bound bromine.

SUMMARY OF THE INVENTION

It is therefore an object of the invention to provide a positive radiation-sensitive mixture which is suitable for use as an electron-beam or X-ray resist, has an increased sensitivity and improved resolution, does not exhibit scumming after development with an aqueous-alkaline developer and has adequate resistance to plasma etching.

These and other objects are achieved by the provision of a positive radiation-sensitive mixture comprising a compound which forms an acid under the action of high-energy radiation, and an acid-cleavable compound, wherein the compound which forms an acid contains aromatically-bound chlorine or bromine and has a $pK_a$ value of less than about 12 or is a derivative of a compound having such a $pK_a$ value.

The present invention also provides a positive radiation-sensitive recording material for high-energy radiation comprising a substrate having a coating of the radiation-sensitive mixture thereon.

A process for producing an imaged recording material comprises the steps of applying a layer of the radiation-sensitive mixture to a substrate, drying the layer, irradiating the dried layer with high-energy radiation, and developing the irradiated layer with an aqueous-alkaline developer to produce an image.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DESCRIPTION OF THE PREFERRED EMBODIMENT

It was entirely surprising that compounds or initiators containing an aromatically-bound chlorine or bromine; and having a $pK_a$ value of less than about 12, or derivatives thereof, have these advantageous properties since the compounds containing aromatically-bound halogen, in particular, bromine, and disclosed in the prior art (DE-A-2,610,842) had not proven suitable.

Of the acid-forming initiators containing aromatically-bound chlorine or bromine, those are preferred which have a pK$_a$ value in the range of about 6 to 10, or are derivatives of these compounds.

The pK$_a$ value of chemical compounds can be determined by customary methods, but theoretical calculations using the "CAMEO" program and the like are also possible.

In addition, the compounds employed as initiators, in contrast to the known initiators, have a low absorption in the spectral region above about 300 nm and thus also allow work to be carried out under conventional laboratory illumination. Compared with the combination, mentioned in EP-A-0,111,274, of brominated poly-p-vinylphenol with initiator compounds which absorb substantially in the region of near UV light above 300 nm, the present invention provides simplified formulations, fewer problems concerning compatibility and finally, by blending with novolaks as binders, the possibility of controlling the development rate, and thus also the radiation sensitivity, as desired.

Suitable acid-forming initiators are those which contain at least one H atom which can be eliminated as a proton in the pK$_a$ range mentioned. These include, in particular, compounds containing carboxyl groups, phenolic OH groups, SH groups or correspondingly activated acid amide groups. However, it is not necessary for these acid groups to be in free form. They may also be protected by suitable protecting groups which can be removed under the processing conditions, for example, acetal, ester and certain ether groups, as present in the acid-cleavable compounds listed below. With certain prerequisites, compounds in which the acid groups mentioned are irreversibly substituted are also suitable initiators. If such compounds are to be employed in aqueous developable mixtures, it is, however, necessary that these mixtures contain substantial proportions of alkali-soluble binders.

Particularly preferred acid-forming initiators are those of the general formula I

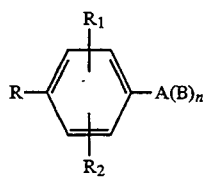
(I)

containing at least one aromatically-bound chlorine or bromine atom, in which:

R denotes carboxyl, OR' or SR',

R$_1$ and R$_2$ are identical or different and denote hydrogen, chlorine, bromine, alkyl which is optionally substituted by aryl, alkoxy, aryloxy or hydroxyl groups or by fluorine atoms; or aryl which is optionally substituted by alkoxy, aryloxy or hydroxyl groups or by halogen atoms, R' denotes hydrogen, alkyl which is optionally substituted by aryl, alkoxy, aryloxy or hydroxyl groups or by fluorine atoms; aryl which is optionally substituted by alkoxy, aryloxy or hydroxyl groups or by halogen atoms; acyl, alkylsulfonyl, arylsulfonyl, alkoxycarbonyl, triorganosilyl, triorganostannyl or denotes an alkylene, arylene, bisacyl, sulfonyl, alkylenedisulfonyl, arylenedisulfonyl, diorganosilyl or diorganostannyl group whose second valency is bonded to the 0 atom of a further unit of the formula I, it being possible for the alkylene and arylene groups to be substituted in corresponding manner to the alkyl and aryl radicals, and n denotes 0 to 3, whereby for n=0:
A denotes hydrogen, chlorine, bromine, alkyl which is optionally substituted by alkoxy, aryloxy, hydroxyl or aryl radicals or by fluorine atoms; or aryl which is optionally substituted by alkoxy, aryloxy, hydroxyl or carboxyl radicals or by halogen atoms, for n=1:
A denotes a single bond, —O—, —S—, —SO$_2$—, —NH—, —NR$_3$—, alkylene or perfluoroalkylene, for n=2:
A denotes

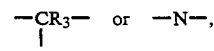

and for n=3:
A denotes

and
B denotes

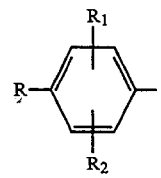

carboxyl, substituted carbonyl, in particular, alkylcarbonyl or arylcarbonyl, carboxyalkyl or substituted sulfonylimidocarbonyl, and R$_3$ denotes alkyl, in particular, (C$_1$–C$_3$)alkyl, or aryl, in particular, phenyl.

It is very particularly preferred when:

R$_1$ and R$_2$ are identical and denote, in particular, bromine, where they are in each case in the ortho position to R, and R is a hydroxyl group which is free or protected by an acid-removable group.

At the same time, it is likewise particularly preferred when:

A (for n=1 and

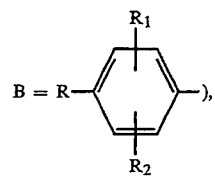

denotes

propylene or perfluoropropylene, the two last mentioned substituents preferably each being substituted on the same carbon atom by

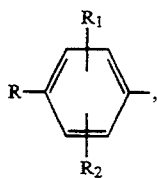

or

A (for n=1 and B=alkylcarbonyl, in particular, methylcarbonyl, carboxyalkyl, in particular, carboxymethyl, or substituted sulfonylimidocarbonyl, in particular, p-toluenesulfonylimidocarbonyl) denotes —O—, —NH— or —NR$_3$—, or A (for n=O) denotes hydroxyl or carboxyl or alkyl which is substituted on each second carbon atom by phenyl, optionally containing one or more bromine atoms.

Likewise particularly preferred are phenolic resins in which some or all of the unsubstituted o- or p-positions relative to the hydroxyl function have been partially or fully chlorinated and/or brominated.

Especially preferred are novolak types which are obtained by condensation of p-bromo-o,o'-bis-methylolphenol and optionally bromine-substituted m-cresol, or those compounds in which some of the phenolic hydroxyl groups are protected by removable groups.

Especially preferred compounds are those in which, for n=0 and A=substituted carbonyl:

R denotes hydroxyl, and

R$_1$ and R$_2$, in each case in the ortho position to R, denote bromine, or for n=0 and A=optionally substituted alkyl:

R denotes hydroxyl, and

R$_1$ and R$_2$, in each case in the ortho position to R, denote hydrogen or bromine.

The content of acid-forming initiators in the radiation-sensitive mixture according to the invention is generally about 2% to 50% by weight, preferably about 4% to 25% by weight, relative to the total weight of the coating.

If the initiator is in polymeric form, in particular, as part of the binder, the upper limit is represented by the contents indicated under the corresponding polymeric binders. The respective content of the initiator or of the molecule groups in the polymer responsible for initiation can be calculated from the mixing ratios of the monomeric starting components.

The following classes of compounds, above all, have proven successful for use as acid-cleavable component in the radiation-sensitive mixture according to the invention:

a) those containing at least one orthocarboxylic ester and/or carboxamide acetal group, it being possible for the compounds to have a polymeric character and for the groups mentioned to occur as linking elements in the main chain or as lateral substituents, b) oligomeric or polymeric compounds containing recurring acetal and/or ketal groups in the main chain, c) compounds containing at least one enol ether or N-acyliminocarbonate group, d) cyclic acetals or ketals of β-ketoesters or -amides, e) compounds containing silyl ether groups, f) compounds containing silylenol ether groups, g) monoacetals or monoketals whose aldehyde or ketone components have a solubility in the developer between 0.1 and 100 g/l, h) ethers based on the tertiary alcohols, and i) carboxylates and carbonates of tertiary, allylic or benzylic alcohols.

As components of radiation-sensitive mixtures, acid-clearable compounds of type a) are described in detail in EP-A-0,022,571 and DE-A-2,610,842; mixtures which contain compounds of type b) are described in DE-C-2,306,248 and DE-C-2,718,254; compounds of type c) are mentioned in EP-A-0,006,626 and 0,006,627; compounds of type d) are presented in EP-A-0,202,196; compounds belonging to e) are presented in DE-A3,544,165 and DE-A-3,601,264; compounds of type f) are found in U.S. patent application Ser. No. 07/243,819 (corresponding to German Patent Application P 3,730,783.5), filed simultaneously, and compounds of type g) are discussed in U.S. patent applications Ser. Nos. 07/243,818 and 07/243,792 (corresponding to German Patent Applications P 3,730,785.1 and P 3,730,787.8), likewise filed simultaneously. Compounds of type h) are described, for example, in U.S. Pat. No. 4,603,101, and compounds of type i) for example, in U.S. Pat. No. 4,491,628 and by J. M. Fréchet et al., J. Imaging Sci., 30: 59–64 (1986). The contents of these references are hereby incorporated by reference.

It is also possible to use mixtures of the acid-clearable materials mentioned. However, an acid-clearable material which belongs to one of the above-mentioned types is preferred. Of the materials, those are particularly preferred which belong to types a), b), g) and i). Under type b), the polymeric acetals should be particularly emphasized; of the acid-cleavable materials of type g), those whose aldehyde or ketone component has a boiling point higher than about 150° C., preferably higher than about 200° C. are preferred.

The content of acid-cleavable material in the radiation-sensitive mixture according to the invention should be about 1% to 50% by weight, preferably about 5% to 25% by weight, relative to the total weight of the coating.

The radiation-sensitive mixture according to the invention may additionally comprise a binder which is insoluble in water, but is soluble, or at least swellable, in organic solvents and aqueous alkali. Such binders include, above all, phenolic resins of the novolak type. Phenol-formaldehyde resins, cresol-formaldehyde resins, and the co-condensates and mixtures thereof are mentioned.

In addition, it is also possible to employ vinyl polymers, such as poly(vinyl acetals), polymethacrylates, polyacrylates, poly(vinyl ethers), polyvinylpyrrolidones and styrene polymers, each of which may optionally be modified by comonomers, which are used alone or mixed with other polymers (polymer blends).

The following may be mentioned in particular: polymers of styrene with alkenyl sulfonyl amino carbonyloxy or cycloalkenyl sulfonyl amino carbonyloxy units (EP-A-0,184,804), polymers of acrylic acid, methacrylic acid, maleic acid, itaconic acid, etc., containing lateral, crosslinking —CH$_2$OR groups (EP-A-0,184,044), polymers made of vinyl monomers and alkenylphenol units (EP-A-0,153,682), polyvinylphenols as novolak substitutes (DE-C-2,322,230), polymeric binders containing lateral, phenolic hydroxyl groups (EP-A-0,212,439 and 0,212,440), styrene-maleic anhydride copolymers (DE-A-3,130,987), polymers made from unsaturated (thio)phosphinic acid iso(thio)cyanates with a polymer containing active hydrogen (DE-A-3,615,612 and 3,615,613), polymers containing vinyl acetate, vinyl alcohol and vinyl acetal units (EP-A0,216,083), and poly(vinyl acetals) containing units of hydroxy aldehydes (DE-A-3,644,162).

The amount of binder is generally about 1% to 90%, in particular, about 5% to 90% by weight, more preferably about 50% to 90% by weight, relative to the total weight of the radiation-sensitive mixture.

The water-insoluble, but alkali-soluble binder mentioned may be omitted, if desired, when polymeric initiators; are used. In particular, brominated polystyrenes or polyvinylphenols are suitable for this purpose. This has the consequence that the content of the polymeric initiator may extend beyond the range described for the initiators. In particular, contents of greater than about 50% by weight and up to about 100% by weight relative to the total weight of the radiation-sensitive mixture, less the content of the acid-cleavable compound, are included.

In addition, it is also possible to prepare the binder by condensation of a chlorine- or bromine-containing aromatic initiator claimed according to the invention with a starting monomer which is known for the preparation of customary binders. The prerequisite is that the acid-forming chlorine- or bromine-containing material contains groups which are capable of condensation or polymerization.

As far as the monomeric components of customary binders are concerned, phenols and cresols, in particular, m-cresol, are primarily preferred for this condensation. The condensation is preferably carried out using approximately equimolar amounts.

In addition to condensation of the chlorine- or bromine-containing initiator with monomeric components of known binders to form a polymeric initiator which simultaneously acts as binder, simple mixing is also possible of a polymeric initiator and customary binders. In particular, bromine-containing styrene derivatives are mixed with novolak resins, preferably in approximately equimolar amounts.

Furthermore, dyes, pigments, plasticizers, wetting agents and levelling agents, but also polyglycols and cellulose ethers, for example, ethylcellulose, may optionally be added to the radiation-sensitive mixtures according to the invention in order to improve specific requirements, such as flexibility, adhesion and gloss.

The radiation-sensitive mixture according to the invention is preferably dissolved in solvents, such as ethylene glycol, glycol ethers, such as glycol monomethyl ether, glycol dimethyl ether, glycol monoethyl ether or propylene glycol monoalkyl ethers, in particular, propylene glycol methyl ether; aliphatic esters, such as ethyl acetate, hydroxyethyl acetate, alkoxyethyl acetate, n-butyl acetate, propylene, glycol monoalkyl ether acetate, in particular, propylene glycol methyl ether acetate, or amyl acetate; ethers, such as dioxane, ketones, such as methyl ethyl ketone, methyl isobutyl ketone, cyclopentanone and cyclohexanone; dimethylformamide, dimethylacetamide, hexamethylphosphoric amide, N-methylpyrrolidone, butyrolactone, tetrahydrofuran, and in mixtures thereof. Glycol ethers, aliphatic esters and ketones are particularly preferred.

The solutions produced using the components of the radiation-sensitive mixture generally have a solids content of about 5% to 60% by weight, preferably up to about 50% by weight.

A radiation-sensitive recording material, essentially comprising a substrate and the radiation-sensitive mixture applied thereto, is also provided according to the invention.

Suitable substrates are all materials of which capacitors, semiconductors, multi-layered printed circuits or integrated circuits are comprised or from which they can be produced. In particular, surfaces which are made of thermally oxidized and/or aluminum-coated silicon material that is optionally doped may be mentioned, including all other substrates which are customary in semiconductor technology, such as, for example, silicon nitride, gallium arsenide and indium phosphide. In addition, the substrates which are known from the manufacture of liquid-crystal displays, such as glass, indium/tin oxide; metal plates and foils, for example, made of aluminum, copper or zinc; bimetallic and trimetallic foils; and electrically nonconductive foils which are vapor-coated with metals, optionally aluminum-coated $SiO_2$ materials and paper, are suitable. These substrates may be subjected to thermal pretreatment and may be superficially roughened, etched or treated with chemicals in order to improve desired properties, such as, for example, hydrophilicity.

In a particular embodiment, the radiation-sensitive mixture can contain an adhesion promoter for better adhesion, which may be contained in the resist formulation or applied between the resist and the substrate. In the case of silicon or silicon dioxide substrates, adhesion promotes of the aminosilane type, such as, for example, 3-aminopropyltriethoxysilane or hexamethyldisilazane, are suitable for this purpose.

Examples of substrates which can be used for the production of photomechanical recording layers, such as printing forms for letterpress printing, planographic printing, screen printing and rotogravure printing, and for the production of relief copies, are aluminum plates, optionally anodically oxidized, grained and/or silicated aluminum plates, zinc plates, steel plates, which have optionally been treated with chromium, and plastic films or paper.

The recording material according to the invention is irradiated imagewise with high-energy radiation; electron-beam or X-ray radiation is preferred.

The layer thickness varies with the field of use and is between about 0.1 and 100 μm, in particular, between about 1 and 10 μm.

The invention furthermore relates to a process for the production of a radiation-sensitive recording material. The radiation-sensitive mixture can be applied to the substrate by spraying, flow-coating, rolling, spin-coating and dip-coating. The solvent is then removed by evaporation, leaving the radiation-sensitive layer on the surface of the substrate. The removal of the solvents can be accelerated, if desired, by heating the layer to temperatures of up to about 150° C. However, it is also possible to initially apply the mixture in the above-mentioned manner to an intermediate substrate, from which it is transferred onto the final substrate material under pressure at elevated temperature. The intermediate substrates used may, in principle, be any materials mentioned as substrate materials. The layer is subsequently irradiated imagewise. High-energy radiation, such as X-ray or electron-beam radiation, is particularly preferred. High-energy synchrotron radiation having doses from about 20 to 200 $mJ/cm^2$ or radiation from an electron-beam scanner is particularly preferred. In the radiation-sensitive layer, an image pattern is subsequently produced by treating the layer with a developer solution which dissolves or removes the irradiated areas of the material.

The developers used are solutions of alkaline reagents, such as, for example, silicates, metasilicates, hydroxides, hydrogen phosphates, dihydrogen phosphates, carbonates or hydrogen carbonates, in particular, of alkali metal ions or ammonium ions, but also ammonia and organic ammonium bases and the like. The content of these substance in the developer solution is generally about 0.1% to 15% by weight, preferably about 0.5% to 5% by weight, relative to the weight of the developer solution.

In order to increase the resistance to mechanical and chemical influences, in particular, to etching media, the developed layers can be heated for some time, for example, about 5 to 40 minutes, at elevated temperature, for example, above 100° C., it being possible for this effect to be further supported by exposure with UV radiation.

The preparation of the aromatic chlorine- or bromine-containing compounds present in the radiation-sensitive mixture according to the invention, some of which are new, is illustrated with reference to the examples below:

Preparation Example 1

Hexafluorotetrabromobisphenol A 0.2 mol of hexafluorobisphenol A (2,2-bis-(4-hydroxyphenyl)-1,1,1,3,3,3-hexafluoropropane) were dissolved in 100 ml of glacial acetic acid while stirring. A solution of 0.8 mol of bromine in 100 ml of glacial acetic acid was added dropwise at a temperature of 30° C. to 60° C., and the reaction mixture was subsequently refluxed until the elimination of HBr was complete. The hot reaction mixture was stirred into 2 l of warm water, the mixture was cooled to room temperature, and the resultant crystals were filtered off under suction. After purification by sublimation, the melting point of the product was determined as 255° C.

Preparation Example 2

1,1,1-tris-(3,5-dibromo-4-hydroxyphenyl)ethane 102 g of tris-(4-hydroxyphenyl) ethane were suspended in a mixture of 500 ml of glacial acetic acid and 250 ml of water. 334 g of bromine were subsequently added dropwise at 10° C. to the stirred suspension. When the reaction of the bromine was complete, 750 ml of water were added, and the precipitated crystals were filtered off under suction. They were washed with water, recrystallized from toluene and subsequently dried. The product had a melting point of 276°–278° C. The NMR spectrum (CDCl$_3$) exhibited the following signals: CH$_3$: $\delta=2.05$ (3H)s; OH: $\delta=5.89$ (3H)s; Phenyl: $\delta=7.1$ (6H)s.

Preparation Example 3

N-(2,4,6-tribromophenyl)-N'-(p-toluenesulfonyl) urea 50 mmol of 2,4,6-tribromoaniline were dissolved in 20 ml of tetrahydrofuran. A solution of 50 mmol of toluenesulfonyl isocyanate in 20 ml of tetrahydrofuran was added dropwise at room temperature, and the stirred reaction mixture was subsequently kept at 40° C. for 3 hours. The precipitated crystals were filtered off under suction. After recrystallization from toluene, the product had a melting point of 230° C.

Preparation Example 4

Oligomer of tetrabromobisphenol A and 1,4-divinyloxybutane 56.6 g of tetrabromobisphenol A are dissolved in 50 ml of tetrahydrofuran (THF), and 14.8 g of divinyloxybutane are added. The mixture is stirred at room temperature for 3 hours, and the readily-volatile components are removed by distillation on a rotary evaporator on a water-pump vacuum. The colorless solid remaining has a melting point of 79° C. and exhibits $^1$H NMR signals at 7.25 ppm (s, arom.), 5.60 ppm (q, acetal) and 1.57 ppm (methyl).

Preparation Example 5

Tetrabromobisphenol A bis-(1-ethoxyethyl ether)

56.6 g of tetrabromobisphenol A are dissolved in 50 ml of tetrahydrofuran, and 15 g of vinyl ethyl ether and of 0.2 g of Amberlyst are then added. The mixture is refluxed for 3 hours, 5 g of potassium carbonate are added at room temperature, and the mixture is stirred for a further hour, then filtered and evaporated. The highly-viscous brown oil remaining exhibits NMR signals at 7.27 ppm (s, arom.), 5.60 ppm (q, acetal) and 1.60 ppm (methyl).

Preparation Example 6

Tetrabromobisphenol A bis-(trimethylsilyl ether)

56.6 g of tetrabromobisphenol A are dissolved in 50 ml of THF. After addition of 40 g of pyridine, 22.5 g of trimethylchlorosilane are added dropwise at room temperature. The mixture is refluxed for one hour and then worked up by shaking with diethyl ether and water. After evaporation of the ether fraction, crystals are obtained which, after recrystallization from isopropanol, have a melting point of 141° C. NMR: 7.26 ppm (s, atom.), 1.60 ppm (s, Me$_3$Si).

Preparation Example 7

Tetrabromobisphenol A bis-tetrahydropyranyl ether 56.6 g of tetrabromobisphenol A are dissolved in 50 ml of THF. After addition of 17.5 g of dihydropyran and 0.25 g of Amberlyst, the mixture is refluxed for 3 hours, cooled, neutralized by addition of 5 g of potassium carbonate, stirred for a further hour, filtered and evaporated to dryness: oil. NMR: 7.27 ppm (arom.), 6.0 ppm (t, acetal), 1.57 ppm (methyl).

Preparation Example 8

Tetrabromobisphenol A bis(tert-butyl carbonate)

13.6 g of tetrabromobisphenol A are dissolved in 50 ml of THF. After slow addition of 2.65 g of sodium hydride (50%), 10.9 g of di-t-butyl carbonate are added dropwise. The mixture is stirred for 4 hours at 60° C., poured into ice water, and extracted by shaking three times with 150 ml of ethyl acetate in each case, and the organic phase is dried and filtered. The crystals obtained after evaporation give a melting point of 172° C. after recrystallization from isopropanol. NMR: 7.22 ppm (arom.), 1.57 ppm (s, 6H), 1.52 ppm (s, 18H).

Preparation Example 9

Tetrabromobisphenol A diacetate 27.2 g of tetrabromobisphenol A are dissolved in 176.6 ml of pyridine. 7.8 g of acetyl chloride are added slowly to this solution with cooling, and the reaction mixture thus obtained is kept at room temperature overnight. The mixture is filtered, poured into ice water and acidified using concentrated HCl. The precipitated ester is filtered off under suction, taken up in methylene chloride, washed with sodium bicarbonate solution and water, dried and evaporated. The product is recrystallized from acetonitrile, m.p.: 169° C., NMR: 7.42 ppm, 2.40 ppm, 1.68 ppm.

Preparation Example 10

Tetrabromobisphenol A dibenzoate

The preparation is analogous to Preparation Example 9, but using benzoyl chloride in place of the acetyl chloride. White crystals (from acetonitrile): m.p. 219° C., NMR 1.75 ppm (6H, methyl), arom: 14H.

Preparation Example 11

Tetrabromobisphenol A dibenzenesulfonate

The procedure is as in Preparation Example 9, but using benzenesulfonyl chloride in place of acetyl chloride. Crystals (from acetonitrile), m.p.: 208° C., NMR: 1.65 (6H, methyl), arom: 14H.

Preparation Example 12

1,1,1-Tris-(4-hydroxy-3,5-di-bromophenyl)ethane tris-(1-ethoxyethyl ether)

The procedure is as in Preparation Example 5, with the difference that bisphenol A is replaced by the compound from Preparation Example 2, and the vinyl ethyl ether is employed in a three-fold molar excess. NMR: 1.17 ppm (t, methyl), 1.57 ppm (d, methyl), 5.57 ppm (q, acetal), 7.10 (s, arom.)

Preparation Example 13

Tetrabromobisphenol A dimethyl ether 54.4 g of tetrabromobisphenol A are dissolved in 200 ml of 5% strength NaOH. 30.3 g of dimethyl sulfate are added dropwise at room temperature, the mixture is stirred at room temperature for one hour and then warmed to 40° C., and 50 ml of concentrated ammonia solution are added. The product is extracted with methylene chloride, and the organic phase is washed, dried and evaporated. NMR: 7.3 ppm (s, arom. 4H), 3.88 ppm (s, CH$_3$O, 6H), 1.6 ppm (s, CH$_3$, 6H).

The use examples below, in which pw denotes parts by weight, are intended to illustrate the invention in greater detail.

Example 1

A coating solution was produced from:

| | |
|---|---|
| 17 pw | of a cresol-formaldehyde novolak having a softening range of 105°–120° C., |
| 5 pw | of a polymeric acetal made from benzaldehyde and hexane-1,6-diol, analogously to the preparation example 19 in DE-C 27 18 254 |
| 4 pw | of tetrabromobisphenol A (15.3% by weight of the total solids) in |
| 74 pw | of propylene glycol methyl ether acetate. |

The solution was spin-coated at 3,000 rpm onto a silicon wafer which had been treated with an adhesion promoter (hexamethyldisilazane). After drying at a 85° C. for 30 minutes in a circulation oven, a coating thickness of 1 μm was obtained. Imagewise irradiation was carried out using synchrotron radiation (BESSY, Berlin, air gap 2 mm) in a dose of 44 mJ/cm$^2$ through a gold-on-silicon mask. The experimental arrangements can be found in A. Heuberger, "X-Ray Lithography", *Microelectronic, Engineering* 3: 535–556 (1985). After exposure, the resist coating was kept at room temperature for 30 minutes. The material was developed using an alkaline developer of the following composition:

| | |
|---|---|
| 5.3 pw | of sodium metasilicate × 9 H$_2$O, |
| 3.4 pw | of trisodium phosphate × 12 H$_2$O, |
| 0.3 pw | of sodium dihydrogen phosphate, and |
| 91 pw | of demineralized water. |

After a development time of 30 s, a flaw-free image containing all details of the mask was obtained. The resist edges were not negatively undercut and exhibited angles of virtually 90° C. (in a photomicrograph from a scanning electron microscope (SEM)).

Example 2

A coating solution and the resist were produced in corresponding manner to Example 1: however, the initiator specified therein was replaced by the same amount of hexafluorotetrabromobisphenol A (Preparation Example 1). The results regarding resolution and angle of resist edges to the carrier material after development using the developer from Example 1 were comparable to those from Example 1.

Example 3

A coating solution was produced in corresponding manner to Example 1. However, the tetrabromobisphenol A was replaced as initiator by bis(3,5-dibromo-4-hydroxyphenyl) sulfone in cyclohexanone as solvent. After exposure, the resist was developed in the developer of Example 1, the development time being reduced to 20 s; results with respect to resolution and resist edges again corresponded to those which were obtained in Example 1.

Example 4

The tetrabromobisphenol A employed in Example 1 was replaced by tetrachlorobisphenol A in a coating solution which otherwise corresponded fully to that of Example 1. The solution was spin-coated (3,000 rpm) onto a silicon wafer provided with an adhesion promoter as in Example 1. After drying for one minute at 110° C. on a hot-plate, a coating thickness, of 1 μm was obtained. The material was irradiated with synchrotron radiation (dose: 22 mJ/cm$^2$). The material was developed within 25 seconds after a waiting time of only 2 minutes using a developer which had been obtained by diluting the developer in Example 1 with demineralized water in the ratio 1:1. Under these conditions, it was possible to achieve structural reproductions as in Example 1.

Example 5 (Comparison Example).

A coating solution was produced as in Example 1, but the tetrabromobisphenol A was replaced by 4-iodophenol. The coating was effected in corresponding manner to Example 1. In this example, however, it was not possible to obtain an image after development as in Example 1, even using synchrotron radiation with a dose of 250 mJ/cm$^2$.

Example 6

This example corresponded to Example 1, with the exception that the initiator specified therein was replaced by 1,1,1-tris-(3,5-dibromo-4-hydroxyphenyl) ethane. Irradiation was effected imagewise with synchrotron radiation with a dose of 30 mJ/cm$^2$. After development as in Example 1, results regarding resolution and angle of the resist edges to the carrier were obtained which corresponded to those from Example 1. In addition, the resist of this example had an improved flow stability.

Example 7

In this example, tetrabromobisphenol A was replaced as initiator by 2,4,6-tribromoacetanilide. All the other parameters corresponded to those of Example 1, with the exception that imagewise irradiation was effected using synchrotron radiation with a dose of 170 mJ/cm$^2$. The results were comparable to those of Example 1.

Example 8

In this example, the initiator employed was N-(2,4,6-tribromophenyl)-N'-(p-toluenesulfonyl) urea, corresponding to the procedure from Example 1. Irradiation was effected with synchrotron radiation with a dose of 160 mJ/cm$^2$. All the other parameters corresponded to those of Example 1. The results with respect to resolution and resist edges were likewise comparable with those of Example 1.

Example 9

The initiator used in Example 1 was replaced in this example by 2,4,6-tribromophenoxyacetic acid. Irradiation was effected using synchrotron radiation with a dose of 160 mJ/cm$^2$. The material was developed using the developer from Example 1, but in this case diluted with fully demineralized water in the ratio 1:1. All the remaining parameters were identical to those from Example 1. A flaw-free image of high resolution as in Example 1 was achieved.

Example 10

This example corresponded to Example 9, with the exception that 3,5-dibromo-4-hydroxybenzoic acid was used as initiator. The results corresponded to those from Example 8.

Example 11

A coating solution was produced containing:

| | |
|---|---|
| 11 pw | of a brominated poly(p-hydroxy)styrene having a bromine content of 50% by weight (commercial product from Maruzen), |
| 11 pw | of the phenolic resin of Example 1, |
| 5 pw | of an acetal made from benzaldehyde and phenoxyethanol in accordance with the preparation procedure given below in |
| 73 pw | of propylene glycol methyl ether acetate. |

In corresponding manner to Example 1, the coating was applied, irradiated and developed. Using synchrotron radiation with a dose of 35 mJ/cm$^2$, the resolving power and behavior of the resist edges were identical to those from Example 1.

Preparation of benzaldehyde diphenoxyethyl acetal 0.5 g of p-toluenesulfonic acid was added with cooling to a mixture of 1 mol of benzaldehyde, 2 mol of phenoxyethanol and 1.1 mol of trimethyl orthofore, ate. The mixture was stirred at room temperature for 2 hours. A water-pump vacuum was subsequently applied to the mixing apparatus, and stirring was continued for 2 hours at each of 20° C., 40° C. and 60° C. The reaction mixture was subsequently passed through a thin-film evaporator at 80° C. and a pressure of 0.1 torr. If necessary, further distillation can take place in the thin-film evaporator at appropriate elevated temperature.

The resultant acetal was stirred with Na$_2$CO$_3$, K$_2$CO$_3$ or basic aluminum oxide to neutralize the acid catalyst. The solid components were removed and the filtrate was evaporated in vacuo. It was possible to employ the acetal in its present form in a recording material. It had a melting point of 22°–24° C.; no CO signal could be detected in the IR spectrum; the NMR spectrum (CDCl$_3$) exhibited an acetal signal at $\delta=5.76$ ppm.

Example 12

A coating solution was produced containing:

| | |
|---|---|
| 22 pw | of a bromine-containing novolak produced from a mixture of 2,6-dimethylol-4-bromophenol and m-cresol (molar ratio 1:1, acidic condensation), |
| 5 pw | of the acetal made from piperonal and phenoxyethanol in |
| 73 pw | of propylene glycol methyl ether acetate. |

Analogously to Example 1, a silicon wafer was coated with the coating solution and dried, subsequently irradiated imagewise with synchrotron radiation with a dose of 81 mJ/cm$^2$ and developed.

The results were comparable to those from Example 1.

Preparation of piperonal bis-phenoxyethyl acetal

In addition to the acid and the solvent from the preparation example in Example 11, 1 mol of piperonal and 2 mol of phenoxy ethanol were initially introduced. In corresponding manner to the description in Example 11, it was possible to isolate an acetal, which was produced as an oil. In the NMR spectrum (CDCl$_3$), it exhibited the characteristic signal for acetals at $\delta=5.66$ ppm.

Example 13

A coating solution was produced containing:

| | |
|---|---|
| 11 pw | of a cresol-formaldehyde novolak having a softening range of 105°–120° C., |
| 11 pw | of brominated poly(p-hydroxy)styrene having a bromine content of 50% by weight, corresponding to Preparation Examples 1 to 3, and |
| 5 pw | of an acetal made from cyclohexanone and phenoxy ethanol, which had been produced in accordance with the preparation instructions from Examples 11 and 12 in |
| 73 pw | of propylene glycol methyl ether acetate. |

In a corresponding manner to Example 1, the coating was applied, irradiated and developed. Results analogous to Example 1 were achieved using synchrotron radiation with a dose of 41 mJ/cm$^2$.

Example 14

A coating solution was produced in corresponding manner to Example 13, with the proviso that the acid-cleavable material employed was, in particular, α,p-bis-trimethylsilyloxystyrene in accordance with the preparation example below. The results were analogous to those from Example 12.

Preparation of α,p-Bis-trimethylsilyloxystyrene 0.72 mol of trimethylchlorosilane and 1 mol of triethylamine were initially introduced in 100 ml of dimethylformamide. 0.35 mol of p-hydroxyacetophenone were added dropwise at room temperature while stirring, and the mixture was subsequently heated at 110° C. for 4 hours while stirring. The reaction mixture was cooled, 100 ml of hexane were added, and the mixture was washed with water. After extraction, the organic phase was subjected to fractional distillation. 19 g of the desired bisether (boiling point: 120° C./4 torr) were obtained in this procedure. In view of the enolic protons at $\delta = 4.19$ and 4.65 ppm, the NMR spectrum showed that the carbonyl groups had been fully converted into enol ether groups.

Example 15

A coating solution was produced containing:

| | |
|---|---|
| 16 pw | of poly(4-tert-butoxycarbonyl)styrene, and |
| 4 pw | of tetrabromobisphenol A in |
| 80 pw | of propylene glycol methyl ether acetate. |

The coating was applied and irradiated in corresponding manner to Example 1.

After irradiation, the material was dried for 30 minutes in a circulation oven at 120° C. The imaged sample was subsequently further processed, again in corresponding manner to Example 1. The results with respect to resolving power and resist edge shape corresponded to those from Example 1.

Example 16

A coating solution was produced containing:

| | |
|---|---|
| 7 pw | of a cresol-formaldehyde novolak having a softening range of 105°-120° C., |
| 7 pw | of brominated poly(p-hydroxy)styrene having a bromine content of 50% by weight, corresponding to preparation Examples 1 to 3, and |
| 3 pw | of an acetal made from 4-ethyl benzaldehyde and phenoxyethanol in corresponding manner to the preparation example below in |
| 83 pw | of propylene glycol methyl ether acetate. |

The coating was applied in corresponding manner to Example 1. After the resist had been dried in a circulation oven in accordance with Example 1, a dry coating thickness of 0.3 μm was obtained.

Imagewise irradiation was effected using an electron beam writer at an acceleration voltage of 50 kV with a radiation dose of 1 μC/cm².

Subsequent development using the developer as in Example 1 at a development time of 30 s gave a flaw-free image with a resolving power of 0.3 μm.

Preparation Of 4-ethylbenzaldehyde bis-phenoxyethyl acetal 1 mol of 4-ethylbenzaldehyde and 2 mol of phenoxyethanol were reacted in accordance with the preparation instructions in Example 11. An acetal having a melting point of 48° C. was isolated. The NMR spectrum (CDCl₃) exhibited a signal for an acetal at $\delta = 5.74$ ppm.

Examples 17–26

Coating solutions containing the initiator compound of Preparation Examples 4 to 13 were produced having the following composition:

| | |
|---|---|
| 17 pw | of a cresol-formaldehyde novolak having a softening range of 105°-120° C., |
| 5 pw | of an acetal made from benzaldehyde, and phenoxyethanol, prepared as described in Example 11, and |
| 4 pw | of the respective initiator in |
| 74 pw | of propylene glycol methyl ether acetate. |

The resist film was produced and the irradiation with X-rays was carried out analogously to Example 1. After development under conditions given in Table 1, structural reproductions were in each case achieved which corresponded to the 0.3 μm structures present on the mask.

The resist edges were not negatively undercut and had an edge angle of virtually 90° when assessed using a SEM.

TABLE 1

| Initiator from Prep. Example | BESSY dose 805 MeV | Developer x) | Development time (s) |
|---|---|---|---|
| 4 | 180 mJ/cm² | 1:1 | 20 |
| 5 | 80 mJ/cm² | 1:0.33 | 30 |
| 6 | 25 mJ/cm² | 1:0 | 60 |
| 7 | 180 mJ/cm² | 1:0 | 50 |
| 8 | 90 mJ/cm² | 1:0.5 | 60 |
| 9 | 75 mJ/cm² | xx) | 20 (addition of surfactant) |
| 10 | 75 mJ/cm² | xx) | 10 (addition of surfactant) |
| 11 | 75 mJ/cm² | 1:0 | 20 (addition of surfactant) |
| 12 | 75 mJ/cm² | 1:0 | 165 |
| 13 | 90 mJ/cm² | 1:0 | 200 | x) Developer from Example 1, diluted with demineralized water in the stated ratio.
xx) Developer as in Example 1, but prepared using only 76.7 pw of demineralized water.

Example 27

The procedure followed was as in Example 17, but with the difference that the initiator used was the compound from Preparation Example 5 and the silyl ether of Example 14 was used as a solution inhibitor. After imagewise irradiation with 90 mJ/cm² and development using the developer of Example 1 diluted 1:0.5, a very good resist pattern was obtained within 60 s.

Example 28

Analogously, a very good resist pattern was obtained when the initiator from Preparation Example 10 and tris-phenoxyethyl orthoformate were used after irradiation with 90 mJ/cm² and development for 150 s in the developer of Example 1.

What is claimed is:

1. A positive radiation-sensitive mixture, consisting essentially of:
   an acid-cleavable compound;
   a compound which forms, under the action of high-energy radiation, an acid which cleaves the acid-cleavable compound; and
   optionally a separate polymeric binder which is insoluble in water but soluble in aqueous alkali; wherein the compound which forms an acid is
   (a) a compound containing aromatically-bound chlorine or bromine, which compound eliminates at least one hydrogen atom as a proton and has a $pK_a$ value of less than 12, or
   (b) a derivative of compound (a) in which the acidic group is protected by a protecting group which can be removed under conditions used to process the radiation-sensitive mixture, and wherein the compound which forms an acid is present in the mixture in an amount of from about 15.3 to 50% by weight, based on the total solids weight.

2. A radiation-sensitive mixture as claimed in claim 1, wherein the acid-forming compound has a $pK_a$ value of about 6 to 10.

3. A radiation-sensitive mixture as claimed in claim 1, wherein the acid-forming compound is a compound of the formula I

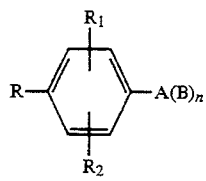

(I)

containing at least one aromatically-bound chlorine or bromine atom, where

R denotes carboxyl, OR' or SR', $R_1$ and $R_2$ are identical or different and denote hydrogen, chlorine, bromine, alkyl which is optionally substituted by aryl, alkoxy, aryloxy or hydroxyl groups or by fluorine atoms; or aryl which is optionally substituted by alkoxy, aryloxy or hydroxyl groups or by halogen atoms, R' denotes hydrogen, alkyl which is optionally substituted by aryl, alkoxy, aryloxy or hydroxyl groups or by fluorine atoms; aryl which is optionally substituted by alkoxy, aryloxy or hydroxyl groups or by halogen atoms; acyl, alkylsulfonyl, arylsulfonyl, alkoxycarbonyl, triorganosilyl, triorganostannyl or denotes a divalent alkylene, arylene, bisacyl, sulfonyl, alkylenedisulfonyl, arylenedisulfonyl, diorganosilyl or diorganostannyl group the second valency of which is bonded to the O atom of a further unit of the formula I, it being possible for the alkylene and arylene groups to be substituted in corresponding manner to the alkyl and aryl radicals, and n denotes 0 to 3, where for n=0:
   A denotes hydrogen, chlorine, bromine, alkyl which is optionally substituted by alkoxy, aryloxy, hydroxyl or aryl radicals or by fluorine atoms; or aryl which is optionally substituted by alkoxy, aryloxy, hydroxyl or carboxyl radicals or by halogen atoms, for n=1:

A denotes a single bond, —O—, —S—, —SO$_2$—, —NH—, —NR$_3$—, alkylene or perfluoroalkylene, for n=2:

A denotes

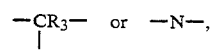

and for n=3:
A denotes

and
B denotes

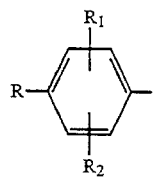

carboxyl, substituted carbonyl, and
R$_3$ denotes alkyl or aryl.

4. A radiation-sensitive mixture as claimed in claim 3, wherein the acid-forming compound has a $pK_a$ value of about 6 to 10.

5. A radiation-sensitive mixture as claimed in claim 3, wherein
   A for n=1 and B=R

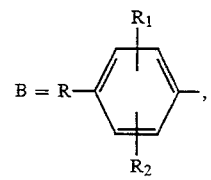

denotes:

propylene or perfluoropropylene or,
A for n=1 and B=alkylcarbonyl denotes —O—, —NH— or —NR$_3$—.

6. A radiation-sensitive mixture as claimed in claim 3, wherein all of the unsubstituted o- or p-positions relative to the hydroxyl function are fully chlorinated or brominated.

7. A radiation-sensitive mixture as claimed in claim 3, wherein B is selected from the group consisting of alkylcarbonyl, arylcarbonyl, carboxyalkyl, and substituted sulfonylimidocarbonyl.

8. A radiation-sensitive mixture as claimed in claim 1, wherein the acid-forming compound is monomeric and the mixture contains a binder which is insoluble in water, but soluble in aqueous alkali.

9. A radiation-sensitive mixture as claimed in claim 1, wherein the acid-forming compound is polymeric.

10. A radiation-sensitive mixture as claimed in claim 9, wherein the acid-forming compound is a hydroxystyrene polymer or copolymer or a phenolic resin.

11. A radiation-sensitive mixture as claimed in claim 9, wherein the mixture additionally comprises a separate polymeric binder which is insoluble in water but soluble in aqueous alkali.

12. A radiation-sensitive mixture as claimed in claim 1, consisting essentially of said acid-forming and said acid-cleavable compound.

13. A radiation-sensitive mixture as claimed in claim 1, wherein the hydrogen atom belongs to a carboxyl, phenolic OH, SH or activated acid amide group.

14. A radiation-sensitive mixture as claimed in claim 1, wherein the compound which forms an acid is present in the mixture in an amount of from about 15.3 to 25% by weight, based on the total solids weight.

15. A radiation-sensitive mixture as claimed in claim 14, wherein the compound which forms an acid is polymeric.

16. A positive radiation-sensitive recording material for high-energy radiation, comprising:
   a substrate; and
   a radiation-sensitive coating on said substrate comprising a positive radiation-sensitive mixture consisting essentially of an acid-cleavable compound; a compound which forms, under the action of high-energy radiation, an acid which cleaves the acid-cleavable compound; and optionally a separate polymeric binder which is insoluble in water but soluble in aqueous alkali; wherein the compound which forms an acid is (a) a compound containing aromatically-bound chlorine or bromine, which compound eliminates at least one hydrogen atom as a proton and has a pK$_a$ value of less than 12, or (b) a derivative of compound (a) in which the acidic group is protected by a protecting group which can be removed under conditions used to process the radiation-sensitive mixture, and wherein the compound which forms an acid is present in the mixture in an amount of from about 15.3 to 50% by weight, based on the total solids weight.

17. A radiation-sensitive recording material for high-energy radiation as claimed in claim 8, wherein the acid-forming compound is a compound of the formula I

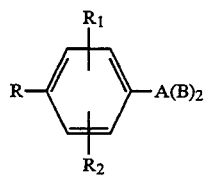

(I)

containing at least one aromatically-bound chlorine or bromine atom, where
   R denotes carboxyl, OR' or SR',
   R$_1$ and R$_2$ are identical or different and denote hydrogen, chlorine, bromine, alkyl which is optionally substituted by aryl, alkoxy, aryloxy or hydroxyl groups or by fluorine atoms; or aryl which is optionally substituted by alkoxy, aryloxy or hydroxyl groups or by halogen atoms,
   R' denotes hydrogen, alkyl which is optionally substituted by aryl, alkoxy, aryloxy or hydroxyl groups or by fluorine atoms; aryl which is optionally substituted by alkoxy, aryloxy or hydroxyl groups or by halogen atoms; acyl, alkylsulfonyl, arylsulfonyl, alkoxycarbonyl, triorganosilyl, triorganostannyl or is a divalent alkylene, arylene, bisacyl, sulfonyl, alkylenedisulfonyl, arylenedisulfonyl, diorganosilyl or diorganostannyl group, the second valency of which is bonded to the O atom of a further unit of the formula I, it being possible for the alkylene and arylene groups to be substituted in corresponding manner to the alkyl and aryl radicals, and
   n denotes 0 to 3, where for n=0:
   A denotes hydrogen, chlorine, bromine, alkyl which is optionally substituted by alkoxy, aryloxy, hydroxyl or aryl radicals or by fluorine atoms; or aryl which is optionally substituted by alkoxy, aryloxy, hydroxyl or carboxyl radicals or by halogen atoms, for n=1:
   A denotes a single bond, —O—, —S—, —SO$_2$—, —NH—, —NR$_3$—, alkylene or perfluoroalkylene, for n=2:
   A denotes

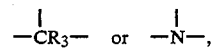

and for n=3:
A denotes

and
B denotes

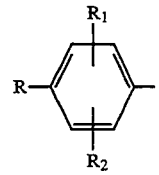

carboxyl or substituted carbonyl, and
R$_3$ denotes alkyl or aryl.

18. A radiation-sensitive material as claimed in claim 17, wherein the acid-forming compound has a pK$_a$ value of about 6 to 10.

19. A radiation-sensitive mixture as claimed in claim 12, wherein R$_3$ is (C$_1$-C$_3$)alkyl or phenyl.

20. A process for the production of an imaged positive radiation-sensitive recording material for high-energy radiation, comprising the steps of:
   applying to a substrate a layer of a positive radiation-sensitive mixture consisting essentially of an acid-cleavable compound; a compound which forms, under the action of high-energy radiation, an acid which cleaves the acid-cleavable compound; and optionally a separate polymeric binder which is insoluble in water but soluble in aqueous alkali; wherein the compound which forms an acid is (a) a compound containing aromatically-bound chlorine or bromine, which compound eliminates at least one hydrogen atom as a proton and has a pK$_a$ value of less than 12, or (b) a derivative of compound (a)

in which the acidic group is protected by a protecting group which can be removed under conditions used to process the radiation-sensitive mixture, and wherein the compound which forms an acid is present in the mixture in an amount of from about 15.3 to 50% by weight, based on the total solids weight;

drying the layer;

irradiating the dried layer imagewise with high-energy radiation to form an acid and cleave the acid-cleavable compound; and developing the irradiated layer with an aqueous-alkaline developer to produce an image.

21. A process as claimed in claim 20, wherein said substrate is coated with an adhesion promoter before applying the radiation-sensitive mixture.

22. A process as claimed in claim 20, wherein the acid-forming compound has a $pK_a$ value of about 6 to 10.

23. A process for the production of an imaged positive radiation-sensitive recording material for high-energy radiation, comprising the steps of:

applying a layer of a positive radiation-sensitive mixture consisting essentially of an acid-cleavable compound; a compound which forms, under the action of high-energy radiation, an acid which cleaves the acid-cleavable compound; and optionally a separate polymeric binder which is insoluble in water but soluble in aqueous alkali; wherein the compound which forms an acid is (a) a compound containing aromatically-bound chlorine or bromine, which compound eliminates at least one hydrogen atom as a proton and has a $pK_a$ value of less than 12, or (b) a derivative of compound (a) in which the acidic group is protected by a protecting group which can be removed under conditions used to process the radiation-sensitive mixture, and wherein the compound which forms an acid is present in the mixture in an amount of from about 15.3 to 50% by weight, based on the total solids weight;

drying the layer;

irradiating the dried layer imagewise with high-energy radiation; and developing the irradiated layer with an aqueous-alkaline developer to produce an image.

* * * * *